United States Patent [19]

Masri et al.

[11] 4,113,567

[45] Sep. 12, 1978

[54] INSOLUBILIZATION OF ENZYMES ON MODIFIED PHENOLIC POLYMERS

[75] Inventors: Merle S. Masri, Emeryville; Virginia G. Randall; William L. Stanley, both of El Cerrito, all of Calif.

[73] Assignee: The United States of America as represented by the Secretary of Agriculture, Washington, D.C.

[21] Appl. No.: 827,659

[22] Filed: Aug. 25, 1977

Related U.S. Application Data

[63] Continuation of Ser. No. 712,298, Aug. 6, 1976, abandoned.

[51] Int. Cl.$^2$ ............................................. C07G 7/02
[52] U.S. Cl. .................................. 195/63; 195/31 R; 195/68; 195/DIG. 11
[58] Field of Search ................... 195/63, 68, DIG. 11, 195/31 R

[56] References Cited

U.S. PATENT DOCUMENTS 3,767,531  10/1973  Olson et al. ........................... 195/63
3,959,080  5/1976  Orth et al. ............................. 195/63

OTHER PUBLICATIONS

Stanley et al., Lactase Immobilization on Phenolic Resins, Biotechnology and Bioengineering, vol. XV, 1973 (pp. 597–602).
Messing, R. A., Immobilized Enzymes for Industrial Reactors, Academic Press, N.Y., 1975 (pp. 101 & 102).

*Primary Examiner*—David M. Naff
*Attorney, Agent, or Firm*—M. Howard Silverstein; David G. McConnell; Theodore J. Leitereg

[57] ABSTRACT

Insolubilized but active enzymes are prepared by mixing an aqueous solution of the enzyme with a modified phenolic polymer. The phenolic polymer is modified by introducing into the polymer chain either aldehyde groups or diazonium salt groups. The so-produced enzyme products retain a substantial part of the original enzyme activity.

6 Claims, No Drawings

INSOLUBILIZATION OF ENZYMES ON MODIFIED PHENOLIC POLYMERS

This is a continuation of application Ser. No. 712,298, filed Aug. 6, 1976, now abandoned.

BACKGROUND OF THE INVENTION

1. Field of the Invention

This invention relates to and has among its objects the provision of novel water-insoluble but active enzyme products and methods for preparing them. Further objects of the invention will be evident from the following description wherein parts and percentages are by weight unless otherwise specified.

2. Description of the Prior Art

In recent years there has been considerable interest in preparing enzymes in insolubilized (sometimes referred to as immobilized) form. Such products enable enzyme-catalyzed reactions to be carried out in a simplified and efficient manner. Typically, the insolubilized enzyme is placed in a cylindrical vessel and a solution of the substrate to be reacted is passed through the enzyme column. The reaction takes place within the column and the effluent liquor contains the reaction products. With this system the enzyme can be used repeatedly for processing fresh batches of the substrate. Various techniques have been advocated for preparing insolubilized enzymes. One procedure is to entrap the enzyme in polymerizing polyacrylamide; another is to adsorb it on insoluble media such as ion exchange resins, alumina, etc.

SUMMARY OF THE INVENTION

In accordance with the invention, insolubilized but active enzymes are prepared from enzymes which are in a normal or native (soluble) state. A phenolic polymer, i.e., a polymer containing one or more phenolic groups, is modified and then treated with the enzyme, which thus becomes insolubilized. The phenolic polymer may be modified in either of two ways: In modification A the phenolic polymer is treated to introduce aldehyde functions in the polymer matrix. In modification B diazotized (diazonium salt) groups are incorporated within the polymer chain.

A primary advantage of the products of the invention is that their activity is retained over long periods of use. Thus, the products of the invention have the advantage not only of being reusable, but also usable under conditions of continuous operations for long periods of time and with large amounts of substrates.

In this respect it is important to note that the products of the invention differ from those products in which an enzyme is merely cross-linked to a phenolic resin by means of glutaraldehyde (as described in U.S. Pat. No. 3,767,531). In the instant products the polymer matrix is modified by actual incorporation of aldehydic functional groups therein. This is not the case in the glutaraldehyde preparation wherein the enzyme is merely precipitated interfacially on the resin carrier. As a result of the process of the invention the enzyme becomes chemically bonded to the polymer matrix. Consequently, the activity of the product is retained for longer periods than in products prepared using glutaraldehyde. Furthermore, the products of the invention will not lose their activity when used in the treatment of proteinaceous materials such as whey. On the other hand, glutaraldehyde products become increasingly less and less active under similar circumstances. This difference in properties is attributable to the fact that in the instant products the aldehyde groups become part of the polymer matrix and are chemically bonded to the enzyme, whereas in the known products the glutaraldehyde merely acts as a cross-linking agent on which the enzyme is interfacially deposited or entrapped. Some of the aldehyde groups on the glutaraldehyde are not associated with the enzyme or with the resin but are left free and reactive. Consequently, protein molecules react with these free aldehyde groups and the active enzyme becomes "buried" within the polymer structure. Since the enzyme is no longer accessible at the surface, a loss of enzyme activity of the immobilized product results.

Another advantage of the product of the invention is that it has a granular texture. Consequently, the instant product acts as its own carrier or support so that it can be formed into a column through whch water and other liquids can percolate readily. This is in sharp contrast to known insolubilized enzymes which are generally amorphous materials that cannot be used directly in a column because liquids will not flow therethrough. These known products require the addition of a carrier such as diatomaceous earth, crushed firebrick, or the like to provide a liquid-permeable mass.

Another advantage of the invention is that the products are afforded by simple procedures using readily-available reactants. No exotic chemicals or complicated procedures are required. Nonetheless, the products retain a significant and sufficient part of the activity of the starting enzyme. In some cases the major part of the original activity is retained.

A further advantage of the invention is that useful products can be prepared from any enzyme source, including pure enzymes, enzyme concentrates, crude enzyme preparations, and even such substances as animal organs, plant parts, microbial cultures, and the like. Important in this regard is that application of the herein-described reactants causes most of the active enzyme to be selectively precipitated even where it is present in minute quantity, e.g., as little as 1 mg. of active enzyme in association with gram quantities of inactive components. Accordingly, the invention provides the means for preparing insolubilized products from enzymes which previously were difficult to insolubilize or which were never insolubilized.

Another advantage of the invention lies in the precise control that one can exercise over the extent and direction of enzymic reactions. This results because of the solid nature and the products of the invention which allows specific amounts to be metered out to suit any particular situation.

Another advantage of the invention is that external forces, such as heat, acid, and the like, which might be detrimental to the enzyme, need not be applied to stop the reaction. It is only necessary to separate the granular product from the solution in order to short-stop the reaction.

A further advantage of the invention is explained as follows: Most enzymes have an optimum pH, that is, a pH value at which the enzyme exhibits maximum activity. We have found that insolubilizing an enzyme in accordance with the invention produces a shift in this optimum pH, generally to a lower value. This particular aspect of the invention is quite important where an acidic food product (e.g., a fruit juice) is to be treated enzymatically, since it yields efficient results with enzymes which normally would operate inefficiently at the low pH provided by the acidic food.

DESCRIPTION OF THE PREFERRED EMBODIMENTS

Modification A: In a first step in the process of the invention in accordance with modification A a phenolic polymer is aldehydically-modified, i.e., the phenolic polymer is treated to introduce aldehyde groups within the polymer matrix. Preferably, the phenolic polymer is aldehydically-modified by reaction with phosphorus oxychloride and dimethylformamide. In this way the polymer matrix becomes formylated, i.e., formyl (aldehydic) groups are introduced therein.

Generally, about 1 to 2 equivalents of phosphorus oxychloride per equivalent of each phenolic unit within the polymer are used, and 1 to 20 parts or more of dimethylformamide are employed per part of phenolic polymer. Usually, the phosphorus oxychloride and dimethylformamide are mixed together and the phenolic polymer added to the mixture, but any order of addition may be followed. It is sometimes desirable to cool the premixed reagents to 0° C. prior to addition of the polymer since the reaction is exothermic. After the reagents and the polymer have been combined, the temperature of the mixture is raised to about 30° to 80° C. The mixture is allowed to stand for 0.1–1.5 hours and then is treated to remove excess phosphorus oxychloride and dimethylformamide. To this end, the mixture may be added slowly to ice water. The product is removed from the water, washed thoroughly with excess water, and then dried. It should be noted that the temperature of and the duration of contact between the phenolic polymer, the phosphorus oxychloride, and the dimethylformamide should not be so great as to damage the phenolic polymer. Other methods for introducing aldehyde groups into the polymer matrix will be evident to those skilled in the art.

Modification B: In the first step of the process of the invention in accordance with modification B, a phenolic polymer is diazotized, i.e., the polymer is treated to introduce diazonium salt groups into the polymer matrix. The exact treatment employed depends on whether or not the phenolic polymer contains amino groups. If not, the polymer must first be nitrated by treatment with tetranitromethane, nitric acid, or the like. If tetranitromethane is used, about 0.3 to 2 parts are employed per part of phenolic polymer. The reaction is conducted at 10° to 25° C. for a period of about from 1 to 15 hours.

Following nitration, the phenolic polymer is reacted with sodium dithionite in the proportion of 1 to 3 parts of sodium dithionite per part of phenolic polymer at a temperature of about 10° to 25° C. for a period of 5 to 60 minutes in order to reduce the nitro groups to amino groups.

After the amino groups have been introduced into the polymer matrix, or, if the phenolic polymer already contains amino groups, the polymer is treated to convert these groups to diazonium salt groups. To this end the polymer can be reacted with 1 to 2 parts of nitrous acid per part of polymer. Nitrous acid is produced generally by mixing sodium nitrite with an acid such as hydrochloric or acetic acid. The temperature of the diazotization reaction is about 0° C. and contact between the reactants is maintained for 0.5 to 1 hour. After the reaction, the diazotized polymer is rinsed thoroughly with water and a phosphate buffer of pH 8 and is ready for reaction with an enzyme.

Other methods for diazotizing the phenolic polymer matrix will be apparent to those skilled in the art.

Phenolic polymers, i.e., polymers containing one or more phenolic groups, which may be used in the process of the invention include both synthetic and natural materials. Synthetic phenolic polymers, by way of illustration and not limitation, which may be used in accordance with the invention include phenol-formaldehyde resins produced by the condensation polymerization of phenol, or a substituted phenol, with formaldehyde under acidic or basic conditions. The resin prepared from phenol and formaldehyde has been shown to contain repeating units of the structure

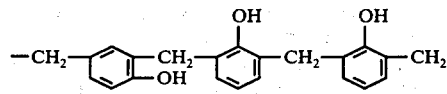

Resins of this type are available on the market under such names as Bakelite and Duolite. Other phenols which may be employed in preparing the resins are listed below by way of illustration and not limitation: Catechol, resorcinol, hydroquinone, o-, m-, and p-cresol, p-hydroxybenzaldehyde, salicylaldehyde, o-, m-, and p-chlorophenol, o-, m-, and p-aminophenol, o-, m-, and p-phenolsulfonic acid, and the like.

For use in the process of the invention, the phenol-formaldehyde resin should be in granular or bead form. If the resin is in large pieces, grinding is applied to reduce it to granular form. It is also desirable to apply a sieving operation to remove fine particles and over-size particles retaining those having a mesh size in the range about from 10 to 40 mesh.

Also prior to use it is preferred to treat the resin to remove impurities. Washing the resin with water is useful for the purpose. A preferred plan involves first washing the resin with distilled water, then soaking it overnight in dilute (about 0.1 M) aqueous NaCl solution, followed by re-washing in distilled water to remove all traces of salt.

Examples of natural phenolic polymers which may be used include wool, silk, and other keratins such as feathers, hoofs, hair, horns, hides, skins, etc., tree bark, nut waste such as skins, pellicles, shells, hulls, expeller meal, certain organic wastes and other humic acid-type materials, etc.

The enzyme to be insolubilized is dissolved or dispersed in distilled water. Where necessary, the pH of the water is adjusted by conventional methods to a level at which the enzyme is soluble. Appropriate pH's to use with any particular enzyme are described in the literature. In many cases a pH of about 3 to 7 is employed. It may further be noted that oftentimes the starting material already contains a buffer or other pH-adjusting agent so that when it is mixed with water the resulting dispersion will exhibit a pH at which the enzyme is most soluble. This is particularly the case with commercially-available enzyme preparations. It is obvious that in such cases there is no need to apply any pH adjustment.

Following preparation of the aqueous solution of the starting material, a mechanical separation step such as filtration or decantation can be applied to remove fillers, debris, or other undissolved material.

Next, the aqueous dispersion of the starting enzyme is added to the modified phenolic polymer. Generally, about 10 to 100 milligrams of crude enzyme per gram of dry modified phenolic polymer are used. The mixture is gently agitated as by shaking, stirring, or the like while being held for about 0.5 to 2 hours at a temperature of about 10° to 25° C. in order to cause the enzyme to become chemically bound to the modified phenolic polymer.

The insolubilized enzyme product is collected by filtration and rinsed several times with distilled water to remove excess reagents and other impurities. The so-prepared enzyme product can be used as is or it may be treated further as described below.

The enzyme product may be mixed with a reducing agent of sufficient reductive capacity to further stabilize and granularize it. It should be obvious that the reducing agent must be selected for its ability to granularize the enzyme product without interfering with the activity of the enzyme. Reducing agents that satisfy this limitation are certain borohydride reducing agents such as sodium borohydride, sodium cyanoborohydride, and the like. Contact between the enzyme product and the reducing agent should be maintained for about 1 to 60 minutes at a temperature of 4°–20° C. or until the desired granular texture has been attained. The concentration of reducing agent depends upon the extent of granularization desired; generally, the concentration of reducing agent is about from 2 to to 10 parts per part of crude enzyme. The above reduction procedure is particularly applicable to the products prepared in accordance with modification A.

During the reduction reaction heat is generated. Consequently, the reaction mixture should be cooled to maintain the temperature between about 4° to 20° C. Following the reduction the product is collected by filtration and washed several times with distilled water to remove excess reagents. The so-prepared insolubilized enzyme is ready for use.

Usually, the starting enzyme contains inactive proteins and other materials and it is desirable to remove these from the final product. To this end the insolubilized enzyme is washed with distilled water for a long period, e.g., about 60 minutes. It is then soaked sequentially in (a) several volumes of 10–15% aqueous sodium chloride, (b) a potassium acetate buffer at pH 7, and, finally, (c) a potassium acetate buffer or other suitable buffer at a pH whereat the enzyme product exhibits maximum activity. The so-prepared and purified product is collected by filtration and is ready for use.

The invention is of wide versatility and can be applied to enzymes of all kinds, illustrative examples being alcohol dehydrogenase, amino acid oxidase, α- and β-amylases, arginase, asparaginase, catalase, cellulase, chymotrypsin, collagenase, deoxyribonuclease, diaphorase, elastin, emulsin, ficin, glucose oxidase, histidase, hyaluronidase, invertase, lactase, peroxidase, phosphatases, lipase, lipoxidase, lysozyme, papain, chymopapain, pepsin, pectic methyl esterase, polyphenol oxidase, rennin, ribonuclease, trypsin, tyrosinase, urease, etc. The starting enzyme need not be a purified substance but may be a preparation containing an enzyme. Thus, for example, one may employ microbial preparations which contain enzymes, typically, cultures or cells of yeasts, molds, bacteria, and the like. Other enzyme-containing preparations which may be applied to the process of the invention are such materials as animal organs, e.g., pancreas, liver, etc., insects and insect parts, barley malt, pineapple, papaya, etc.

The products of the invention can be utilized in a variety of ways. A few examples are provided below by way of illustration and not limitation. Whey, currently a waste material in the production of cheese, can be converted efficiently to glucose and galactose, which are useful as fermentation media and the like, by contacting the watery whey with an insolubilized lactase product prepared in accordance with the invention. An insolubilized protease enzyme can be employed to prevent turbidity in beer, wine, fruit juices, etc. Other applications include hydrolyzing starch to glucose, inverting sucrose solutions for the manufacture of candy, conversion of glucose to fructose, de-glucosing egg whites, conversion of dilute alcohol solutions to vinegar, etc.

It is believed that formation of the products of the invention involves the following mechanism. The polymer matrix is modified by the introduction therein of either aldehyde groups or diazonium salt groups. Subsequently, in polymers modified according to procedure A, the enzyme is coupled to the modified polymer matrix by means of Schiff-base formation. Part of the lysyl residues and other free amino groups of the enzyme become bonded to the modified phenolic polymer. In this way the enzyme becomes attached to a "rigid backbone." When the insolubilized enzyme product is treated with a reducing agent, the Schiff-base polymer matrix is reduced and further stabilized, usually yielding a more granularized product. In products prepared in accordance with modification B, on the other hand, the enzyme reacts through its histidyl and, to some extent, its tyrosyl residues with the diazonium salt groups of the modified polymer. However, regardless of the mechanism, the enzymes do become insolubilized and are not removed from the product during use. Thus, it is not meant to limit the invention to a particular mechanism involved in the formation of the product.

EXAMPLES

The invention is further demonstrated by the following illustrative examples.

EXAMPLE 1

Preparation of Lactase Insolubilized on an Aldehydically-modified Phenolic Polymer A mixture of 1.8 moles (140 ml.) of dimethylformamide and 0.8 mole (75 ml.) of phosphorus oxychloride was prepared. Duolite S-30 resin (a phenol-formaldehyde resin produced by Diamond Shamrock Co., Redwood City, Calif.) was dried at 80° C. for 15 hours and added to the above mixture (40 g.). The resulting material was cooled to 0° C. and then the temperature was allowed to rise to 70° C. The temperature was maintained at 70° C. for 1 hour. The slurry was then poured slowly over crushed ice to allow gradual decomposition of the phosphorus oxychloride. (The reaction with the ice is exothermic, consequently care must be taken during the decomposition.) The product was washed thoroughly with water and dried at 70° C. for 15 hours. The yield of aldehydically-modified polymer was 46 g.

A solution of 10 mg. of commercial grade lactase (a β-galactosidase) in 5 ml. of water was prepared. The crude enzyme hydrolyzed about 10 micromoles of lactose per mg. per minute at pH 4 and 40° C. The aldehydically-modified polymer (0.5 g.) was added to the aqueous lactase solution. The mixture was stirred for 1 hour.

The insolubilized enzyme product was separated from the reaction mixture by filtration and washed with distilled water several times. The immobilized enzyme product exhibited an activity of 50 micromoles per minute per gram of moist product. The activity was determined in a shaker bath batch test at 40° C. with 25 ml. of 0.5 M lactose solution in 0.1 M potassium acetate buffer.

EXAMPLE 2

Preparation of Lactase Insolubilized on Aldehydically-modified Wool

A mixture of 60 ml. of phosphorus oxychloride and 350 ml. of dimethylformamide was prepared. Native wool (13.9 g. at ambient temperature and humidity) was dried at 80° C. for 1 hour to give 12.6 g. of dry wool, which was added to the above mixture. The reaction temperature was raised to 70° C., whereat the temperature was maintained for 0.5 hour. The mixture was poured slowly over ice to decompose the phosphorus oxychloride. The product was washed thoroughly with water and dried at ambient temperature and humidity to give 14.2 g. of modified wool.

The modified wool (1.0 g.) was added to a solution of 14 mg. of commercial grade lactase (Example 1) in 7 ml. of water buffered at pH 7.2 (0.1 M disodium hydrogen phosphate and 0.1 M potassium dihydrogen phosphate buffer). The mixture was stirred for 1 hour at ambient temperature (20° C.).

The product was separated from the reaction mixture and washed with distilled water several times. The immobilized enzyme product exhibited the following activity (determined as in Example 1): 9.5 micromoles of glucose formed per minute per g. of modified wool.

EXAMPLE 3

Preparation of Invertase Insolubilized on Aldehydically-modified Wool

A 0.1 ml. sample of a solution of yeast invertase in glycerol (commercially available from SuCruvert Corporation, New York, N.Y.) was diluted with 2 ml. of disodium hydrogen phosphate (0.1 M). To this solution was added 0.68 g. of aldehydically-modified wool (from Example 2). The mixture was stirred at ambient temperature (20° C.) for 1 hour and the product was recovered as described in Example 2.

The activity of the insolubilized enzyme product was determined in a shaker bath batch test at 40° C. with 25 ml. of 0.1 M sucrose solution in 0.1 M disodium hydrogen phosphate and potassium dihydrogen phosphate buffer at pH 5.0 and was found to be 23 micromoles glucose per minute per gram of moist product. The activity of the starting enzyme solution, determined in the same manner was 5000 micromoles glucose per minute per ml.

EXAMPLE 4

Preparation of Lactase Insolubilized on Diazotized Phenolic Polymer

Duolite S-30 resin (Example 1), 15 g., was treated with 5 ml. (8.1 g.) of tetranitromethane in 75 ml. of Tris-HCl buffer [2-amino-2-(hydroxymethyl)-1,3-propanediol hydrochloride] at pH 7.6 and 100 ml. of ethanol. The mixture was stirred at 20° C. for 15 hours. The product was washed thoroughly with 500 ml. each of water, ethanol, 0.5 M potassium dihydrogen phosphate, 0.5 M disodium hydrogen phosphate, water, and methanol. The product was filtered and sucked dry using a water aspirator.

The nitrated resin was reacted with 10 g. of sodium dithionite in 400 ml. of 0.2 M disodium hydrogen phosphate buffer for 15 hours at ambient temperature (20° C.). The product was washed thoroughly with 500 ml. each of water and methanol and then was dried in air. Nitrogen content (determined by Kjeldahl method) was 1.19% as compared with 0.1% for the starting resin prior to nitration.

The above material (1-g. portion) was treated with 0.2 g. of sodium nitrite dissolved in 2 ml. of water and added dropwise to 8 ml. of 3 N HCl (nitrous acid is produced by this combination) for 1 hour at 0° C. The product was washed thoroughly with water and 0.1 M phosphate buffer, pH 8.0.

The moist diazotized resin (1-g. portion containing about 50% water) was reacted with 38 mg. of crude lactase (activity = 12.6 micromoles of glucose per mg. per minute) in 6 ml. of water for 1 hour at 20° C. The immobilized enzyme was separated from the reaction mixture and washed thoroughly with water, then with Tris-HCl buffer, pH 7.6, followed by potassium acetate buffer, pH 4.0, and stored.

The activity of the product was determined as described in Example 1 and was found to be 275 micromoles of glucose per g. of moist product per minute (58% retention of activity).

EXAMPLE 5

Continuous Use of Lactase Insolubilized on a Diazotized Phenolic Polymer

Lactase immobilized on a diazotized phenolic polymer (10 g.) prepared as described in Example 4 was packed into a 1.2 cm. × 18 cm. jacketed column over a bed of sand.

An aqueous lactose solution (4% in 0.1 M potassium acetate buffer, pH 4) was then pumped through the column at varying flow rates. The column temperature was regulated by passing warm water through the column jacket. The extent of hydrolysis was determined by analyzing for glucose in the effluent. The results are summarized below:

| Temperature (° C.) | 35 | | 45 | |
| --- | --- | --- | --- | --- |
| Flow (ml/min.) | 30 | 120 | 30 | 120 |
| Hydrolysis (%) | 60 | 40 | 70 | 50 |

EXAMPLE 6

Preparation of Invertase Insolubilized on Diazotized Phenolic Polymer

Diazotized Duolite S-30 was prepared as described in Example 4 (2 g. moist resin containing 50% water) and added to 0.1 ml. of the yeast invertase solution described in Example 3 diluted with 3 ml. of 0.1 M disodium hydrogen phosphate. The mixture was stirred at ambient temperature (20° C.) for 1 hour and the product was recovered as described in Example 4. The activity of the immobilized enzyme product, determined as in Example 3, was 40 micromoles glucose per minute per gram of moist product (16% of the original enzyme activity).

Having thus described our invention, we claim:
1. A process for preparing an insoluble but active enzyme, which consists of
   (a) dissolving a soluble active enzyme in water,
   (b) mixing the resulting solution with a diazotized phenol-formaldehyde polymer, and
   (c) separating the resulting insolubilized enzyme product from the reaction mixture.

2. The process of claim 1 wherein the diazotized phenol-formaldehyde polymer is prepared by reacting a phenol-formaldehyde polymer with tetranitromethane, followed by sodium dithionite, followed by nitrous acid.

3. The process of claim 1 wherein the enzyme is a sugar-hydrolyzing enzyme.

4. An insoluble but active enzyme, consisting of a soluble enzyme bound to a diazotized phenol-formaldehyde polymer.

5. The product of claim 4 wherein the diazotized phenol-formaldehyde polymer is prepared by reacting a phenol-formaldehyde polymer with tetranitromethane, followed by sodium dithionite, followed by nitrous acid.

6. The product of claim 4 wherein the enzyme is a sugar-hydrolyzing enzyme.

* * * * *